US007889337B2

(12) United States Patent
Al-Jaroudi et al.

(10) Patent No.: US 7,889,337 B2
(45) Date of Patent: Feb. 15, 2011

(54) OPTICAL METHOD FOR DETERMINATION OF THE TOTAL SUSPENDED SOLIDS IN JET FUEL

(75) Inventors: Said S. Al-Jaroudi, Al-Qatif (SA); Rashed A. Hadi, Tanajib (SA); Amer A. Al-Shahri, Dammam (SA)

(73) Assignee: Saudi Arabian Oil Company (SA)

( * ) Notice: Subject to any disclaimer, the term of this patent is extended or adjusted under 35 U.S.C. 154(b) by 91 days.

(21) Appl. No.: 12/506,001

(22) Filed: Jul. 20, 2009

(65) Prior Publication Data

US 2011/0013184 A1    Jan. 20, 2011

(51) Int. Cl.
*G01N 15/02* (2006.01)
(52) U.S. Cl. ..................................... 356/338
(58) Field of Classification Search .......... 356/335–343
See application file for complete search history.

(56) References Cited

U.S. PATENT DOCUMENTS

| | | | |
|---|---|---|---|
| 3,614,433 A | 10/1971 | Caldwell | |
| 4,918,979 A | 4/1990 | Pearce et al. | |
| 5,468,262 A | 11/1995 | Acker et al. | |
| 5,553,616 A | 9/1996 | Ham et al. | |
| 5,715,046 A | 2/1998 | Tolvanen et al. | |
| 6,064,480 A | 5/2000 | Mountain et al. | |
| 6,178,383 B1 * | 1/2001 | Pegram et al. | 702/25 |
| 6,691,557 B1 | 2/2004 | Rice | |
| 6,881,760 B1 | 4/2005 | Smith et al. | |
| 7,167,776 B2 | 1/2007 | Maharajh et al. | |
| 7,224,455 B2 | 5/2007 | Myers et al. | |
| 2003/0154044 A1 | 8/2003 | Lundstedt | |
| 2007/0086008 A1 * | 4/2007 | Schweighardt et al. | 356/337 |
| 2007/0237679 A1 | 10/2007 | Hegazi | |
| 2008/0156073 A1 * | 7/2008 | Burns et al. | 73/23.35 |

FOREIGN PATENT DOCUMENTS

| | | |
|---|---|---|
| EP | 1715323 A1 | 10/2006 |
| GB | 1460623 | 1/1977 |

OTHER PUBLICATIONS

V.N. Zrelov et al., "Method for Determination of Content of Particulate Contaminant in Jet Fuels", Chemistry and Technology of Fuels and Oils, 1979, pp. 620-623, vol. 15, 1980 Plenum Publishing Corporation.
International Search Report for PCT/US2010/041974 dated Nov. 9, 2010.

* cited by examiner

*Primary Examiner*—Hoa Q Pham
(74) *Attorney, Agent, or Firm*—Bracewell & Giuliani LLP

(57) ABSTRACT

The invention provides a method for the quantitative determination of total suspended solid particles in a liquid. The method includes providing a liquid sample that includes solids suspended therein, illuminating the solids with a light source, collecting light scattered by the solids and correlating the light scattered by the solids with a total solids content.

18 Claims, 5 Drawing Sheets

US 7,889,337 B2

OPTICAL METHOD FOR DETERMINATION OF THE TOTAL SUSPENDED SOLIDS IN JET FUEL

FIELD OF THE INVENTION

The invention relates to a method and apparatus for determining a solids content in a hydrocarbon liquid. More particularly, the invention relates to an optical method for determining the total suspended solids content in a hydrocarbon liquid, such as for example, aviation fuel.

BACKGROUND OF THE INVENTION

The aviation jet fuel that is used in turbine engines is a hydrocarbon typically manufactured from straight-run kerosene. Exemplary jet fuels include commercial jet fuels including Jet A, Jet A-1 and Jet B type fuels and military aircraft jet fuels including JP-1, JP-4, JP-5, JP-6, JP-7, JP-8 and JPTS. The quality of the jet fuel directly effects aviation safety. Particulate matter present in aviation fuels are most frequently products of solid corrosion (e.g., rust and scale buildup), although catalyst fines, salts and other solids may also contribute to the total amount of suspended particulate matter present in the fuel. A determination of the total suspended solids present in the jet fuel is an essential specification in determining the quality of the fuel. The presence of particulate matter in aviation fuel can increase wear and tear on the precision parts in a jet engine, clog fuel equipment and can cause a wide range of mechanical engine malfunctions, such as for example, filter plugging and other operational problems.

To date, the sole quantitative approved method that has been utilized to determine the total suspended solids present in aviation jet fuels is a gravimetric method that includes the filtration of the solids present in the fuel (as described in ASTM D-5452). This method, however, suffers in that the method is time consuming, frequently requiring four hours or more per sample to complete, requires large amounts of aviation fuel to provide sufficient particulate matter for accurate measurement, for example, at least 3 L, preferably at least 4 L, of the aviation fuel, and requires a specialized metallic container, which is expensive, for collection to the fuel samples. Typically, the allowable limit of total suspended solids in aviation fuel is 1.00 mg/L. Prior art gravimetric techniques have been found to have an average error of approximately 0.02 mg/L.

The use of optical analysis techniques to estimate the total suspended solid content as a volume ratio of the suspended solid to the volume of the jet fuel has been previously described. The prior art optical method, however, first determines a volume to volume ratio of solids to fuel, which is then converted to a weight to volume ratio using an arbitrary density value for the suspended solids. This method, in using an arbitrary assumed density for the particulate matter, provides only an approximate value for the total suspended solids, and cannot be considered an accurate quantitative measurement. Generally, prior art methods can have an error of up to 25% or more of the actual total suspended solids value, which is too large to be considered an accurate measurement because the allowable limit of total suspended solids is only 1.00 mg/L. The inaccuracy of the prior art method is due in part because the method relies heavily upon an estimated density of the suspended particulate solids.

Thus, there exists a need to develop a simple and quick method for the accurate determination of weight per unit volume of solids suspended in jet fuel.

SUMMARY

The invention provides a method and system for the determination of total suspended solids in a jet fuel sample.

In one aspect, a method for the quantitative determination of solid particles in a hydrocarbon liquid is provided. The method includes providing a hydrocarbon liquid sample that includes solid particles suspended therein, illuminating the solid particles with a light source, detecting light scattered by solid particles; and correlating the light scattered to a total solids content of the hydrocarbon liquid sample, to determine a calculated total suspended solids In certain embodiments, the method further includes applying a correction factor to the calculated total suspended solids to determine a corrected total suspended solids, wherein the correction factor is determined by correlating optical measurement of the volume of solids present in the hydrocarbon liquid sample and gravimetric measurement of the mass of solids present in the hydrocarbon liquid sample.

In another aspect, a method for determining the amount of solids in a hydrocarbon liquid that contains solid particles suspended therein is provided. The method includes the steps of providing a hydrocarbon liquid sample of known volume, wherein the hydrocarbon liquid sample includes an unknown quantity of solids suspended therein. The hydrocarbon liquid sample is subjected to a light source, such that light from the light source scatters as a result of contacting the solid particles suspended in the hydrocarbon liquid sample. The scattered light is detected with a photodetector, and the photodetector produces a signal corresponding to the scattered light. The signal produced by the photodetector corresponds to a volume of solid particles suspended in the hydrocarbon liquid sample. The signal is subjected to a correction factor, wherein the correction factor providing a mass for the solid particle suspended in the hydrocarbon liquid sample.

In another aspect, a system for determining total suspended solids in a hydrocarbon liquid sample is provided. The system includes a first computer, a light source, a light detector and a sample holder, wherein the first computer is configured to send and receive signals to a light source and light detector and display a resultant total measured suspended solids value. Additionally, the system includes a computer program product associated with the light source and light detector, which is stored on a tangible computer memory media and operable on a computer. The computer program product includes a set of instructions that, when executed by the computer, cause the computer to perform various operations. The computer receives an indication that a hydrocarbon liquid sample containing suspended solids therein is positioned in a sample holder and ready to be measured. In response to the computer receiving the indication that the hydrocarbon liquid sample is positioned in the sample holder, the computer sends a signal from the computer to the light source to illuminate the hydrocarbon liquid sample with the light source. The light source is positioned such that the light source is capable of illuminating the sample holder, wherein light that contacts solids that are suspended in the hydrocarbon liquid sample creates a scattered light pattern. The computer receives a signal from the light detector, wherein the signal is a measure of the collected scattered light. The signal corresponds to a volume of suspended solids in the hydrocarbon liquid sample that results from the measurement the scattered light by the light detector. The step of measuring the scattered light is responsive to an indication received by the light detector from the computer that the hydrocarbon liquid sample is being illuminated with the light source. The light detector is proximate to the sample holder and operable to measure the light scattered by the suspended particles in the hydrocarbon liquid sample. The computer correlates the signal from the light detector to a mass of total suspended solids in the hydrocarbon liquid sample, by correlating the signal in a step that includes utilizing a predetermined average density of the suspended solid particles. The computer communicates the mass of total suspended solids in the hydrocarbon liquid sample to an operator.

In another aspect, a computer program product, which is stored on a tangible computer memory media and operable on a computer, is provided. The computer program product includes a set of instructions that, when executed by the computer, cause the computer to perform the following operations. The computer receives instructions that a hydrocarbon liquid sample containing suspended solids therein is positioned in a sample holder and ready to be measured. The computer sends a signal to the light source to illuminate the hydrocarbon liquid sample with the light source, the step of sending of the signal being responsive to the computer receiving the instructions that the sample is positioned in the sample holder. The light source is positioned such that the light source is capable of illuminating the sample holder, such that the light from the light source contacts solids that are suspended in the hydrocarbon liquid sample to create a scattered light pattern. The computer receives a signal from the light detector, the signal being a measure of the collected scattered light, said signal corresponding to a volume of suspended solids in the hydrocarbon liquid sample, and the signal resulting from the measurement the scattered light by the light detector. The step of measuring the scattered light is responsive to an indication received by the light detector from the computer that the hydrocarbon liquid sample is being illuminated with the light source. The light detector is proximate to the sample holder and operable to measure the light scattered by the suspended particles. The signal from the light detector is correlated by the computer to a mass of total suspended solids in the hydrocarbon liquid sample, the step of correlating the signal comprising utilizing a predetermined average density of the suspended solid particles. The computer communicates the mass of total suspended solids in the hydrocarbon liquid sample to an operator.

In certain embodiments, the operator inputs instructions that the hydrocarbon liquid sample is positioned in the sample holder and ready to be measured. In other embodiments, a sensor electronically coupled to the sample holder and configured to determine when a sample is positioned in the sample holder communicates to the computer that the hydrocarbon liquid sample is in the sample holder and ready to be measured. In certain embodiments, the correction factor is determined by correlating an optical determination of total volume of suspended solids in a hydrocarbon liquid sample and a gravimetric determination of a total mass suspended solids in the hydrocarbon liquid sample.

DETAILED DESCRIPTION OF THE INVENTION

Figure 1:
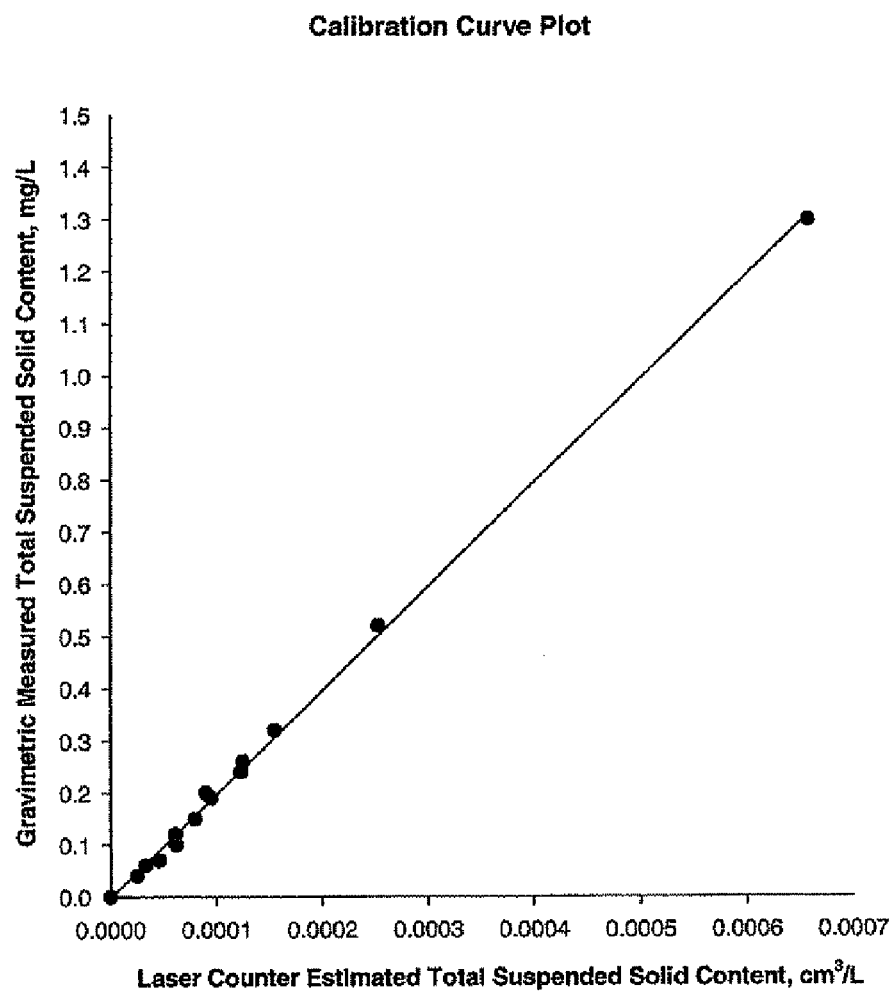
FIG. 1 shows a calibration curve for determination of total suspended solid content according to one embodiment of the present invention.

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein are set forth without any loss of generality to, and without imposing limitations thereon, the claimed invention.

One aspect of the present invention provides optical methods for the simple and quick determination of the total suspended solids content in liquid samples. Exemplary liquid samples can include liquid hydrocarbons, such as aviation fuel. The inventive methods typically require a single instrument calibration for quantitative measurements. The current ASTM industry standard for the determination of suspended solids in aviation fuel utilizes a gravimetric method for the determination of the total suspended solids content, requiring substantially large liquid samples of aviation fuel (e.g., 3-4 L) that must be filtered and dried to determine the overall solids content, and must be conducted under laboratory conditions. In contrast, embodiments of the present invention provide an instrument which requires substantially smaller samples, relative to what is required for the gravimetric method, and is capable of being used under either field or laboratory conditions, or can be integrated with process or delivery equipment for in-line monitoring of the total suspended solids in a liquid.

In one aspect, an apparatus is provided for the quantitative determination of solids in a hydrocarbon liquid sample, such as, aviation fuel. The apparatus includes a sample holder, a light source, a light detector, and a computing device operable to control the apparatus and calculate total overall suspended solids in the hydrocarbon liquid sample. The apparatus is configured such that the sample holder is positioned such that the light source can directed at the sample holder. Additionally, the light detector can be configured to detect light scattered by particulate matter present in the sample holder. In certain embodiments, the apparatus can be configured such that at least one of the light source and the light detector is rotated about the sample holder. In other embodiments, the apparatus can be configured such that the light source and light detector remain stationary and the sample holder is rotated. The associated computing device can be configured to provide instructions to the light source and the light detector. Optionally, the computing device is configured to receive and process data in the form of signals received from the light detector, and is further configured to provide and optionally display an end result of total suspended solids in the hydrocarbon liquid sample.

In another aspect of the present invention, a method is provided for the quantitative determination of the total suspended solids content in the hydrocarbon liquid, such as aviation fuel. The method includes the use of optical means, such as, the use of a laser particle counter, to provide data relating the size and distribution of solids in the hydrocarbon liquid. The particle size and distribution data collected can be correlated to a predetermined density for the solid particles to provide quantitative determination of the mass of solids present in the hydrocarbon liquid sample. The gravimetric method is employed to provide calibration of the laser particle counter and provide more accurate determination for the total suspended solids content as weight of the total suspended solid to the hydrocarbon liquid volume.

The method includes the step of providing the hydrocarbon liquid sample to the apparatus. Total volume for the hydrocarbon sample can be less than 100 mL, which is sufficient to provide multiple samples. In one embodiment, the present invention provides a method for determining a total suspended solids content that requires less than about 50 mL of sample, preferably less than about 25 mL of sample, and more preferably less than about 10 mL of sample. Sampling is done at ambient temperature, preferably between about 20° and 30° C. Utilizing the optical methods and an associated analysis module described herein, routine sample preparation and analysis typically takes less than about 10 minutes, preferably less than about 5 minutes, for the determination of the total suspended solids content.

The method also includes the step of detecting solid particles by optical means This can include providing the light or laser source, which is used to provide a laser light source or laser light beam, which contacts the solid particles. In certain embodiments, the amount of the suspended solids in the liquid sample is measured using a near angle light scatter principle, wherein a revolving laser beam passes through the walls of a sample holder or glass window of a flow-thru cell. The laser source can be a basic light from a laser diode able to be filtered and focused using known materials, such as a lens assembly, to form a small and well-defined illuminated volume of liquid being tested. Optionally, the laser source can be a common p-n junction laser diode including, for example, gallium-arsenide or other semiconductor chips, suitable to produce small packages of coherent light. In certain preferred embodiments, the laser light source has a wavelength of about 650 nm. Optionally, the laser light source can include a high energy laser source, such as helium, neon, argon, Nd-YAG, or the like, which can provide higher sensitivity for certain applications, such as, turbid samples or samples contaminated with oil. The forward scattering interference patterns created by illuminating the particles with a beam of monochromic light are analyzed to provide a measure of the suspended particles. Preferably, the total suspended solids is measured by using a laser particle counter, such as for example, a Spectrex PC-2000, which provides uncorrected total suspended solids values, including the number of particles and the volume of the particles, that can then be correlated with values determined using the gravimetric method.

Scatter is a measure of the quantity of optical energy scattered by the particulate matter. Backscatter refers to scatter that is detected approximately 180° away from the projected beam and forward scatter refers to scatter that is detected at or about the same angle as the projected light beam. Backscatter typically responds well in low concentration samples, or samples with small particles. Forward scatter also responds well to low concentration samples, and advantageously minimizes errors associated with color, size and shape of the particles.

Light from the light source measures a cross-sectional dimension of particles suspended in a liquid by the scattering of light. For example, the laser diode can be directed at the sample container, which can include the hydrocarbon liquid having suspended particles therein, and rotated at a constant rate, thereby illuminating a specified volume of liquid that includes an amount of sediment suspended therein. As the laser beam strikes individual particles suspended in the liquid, the light is scattered. This scattered light can then be collected by the light detector, The light detector causes an electrical pulse to be generated in a preamplifier, which corresponds to the volume of the illuminated particle. In other embodiments, the sample holder or sample container can be rotated and at least one of the laser diode or light detector can remain stationary.

The light detector can be a known device, such as for example, a photodetector, a photodiode or charge coupled device. In certain embodiments, the light detector is configured to detect forward scatter. In embodiments configured to detect forward scatter, the light detector can be configured to detect light that is scattered at between about ±10°, preferably ±5° from the incident beam. In other embodiments, the light detector is configured to detect back scatter. In embodiments configured to detect back scatter, the light detector is configured to detect light that is scattered at an angle of between about 180°±10° to the incident beam. Optionally, the light detector can include focusing optics configured to improve the signal to noise ratio. Optionally, the light detector can include one or more filters or amplifiers.

The sample container can be any apparatus designed to hold the hydrocarbon liquid sample, including, for example, aviation jet fuel The sample container is preferably formed from an optically transparent and chemically inert material, such as quartz, fused silica, or any other material having a high transmittance to ultraviolet radiation (UV), and may be in the form of a conventional cuvette, test tube, or the like. Preferably the optical path is consistent for the sample container. Optionally, the apparatus can include a heater for heating the liquid hydrocarbon sample.

In certain embodiments, the accuracy of the laser particle counter in determining the amount of total suspended solids in a hydrocarbon liquid sample can be improved by applying statistical methods designed to identify and remove data points that fall outside of certain predetermined parameters. In certain embodiments, Dixon or box plot (also known as boxplot) tests can be applied to the analysis results. In certain embodiments, in an effort to improve the signal to noise ratio prior to signal process, the method can include the steps of running multiple scans per sample and averaging the results.

In certain embodiments, the present invention provides a batch process, wherein the hydrocarbon liquid sample is physically extracted from a production process and provided to a separate stand alone analysis unit. In other embodiments, the analysis unit can be integrated inline in a hydrocarbon production process unit, such as an aviation fuel production unit.

In certain embodiments, the apparatus for the optical determination of solids in the hydrocarbon liquid sample, including the laser particle counter, can be configured to operate as an in-line analysis step for a chemical process. For example, the apparatus can be positioned at one or more locations of a hydrocarbon cracking process to determine total solids present.

In certain embodiments, a masking agent can be added to the solution to prevent water from being mistaken for suspended solids, thereby providing false positive measurements. Exemplary masking agents are known in the art, and can include mixtures of toluene and primary and secondary alcohols, such as propanol and isopropanol.

In addition to the components described herein, in certain embodiments, the apparatus for determining total suspended solids includes a computing device selected from one or more networked personal computer, laptop, server, or the like. The computing device can include one or more correlation module for performing various calculations including correlations, corrections, or statistical methods. The computing device can include computer instruction code, such as for example, Java, C, C++, Visual Basic, and the like. The software code can be stored as a series of instructions or commands on a readable computer medium, including random access memory, read only memory, a magnetic medium, such as for example, a hard drive or floppy disc, an optical medium, or like device. In addition, the computing device can include software operable to provide results related to absolute particle counts, mean particle size, mass distribution, percentage distribution, total suspended solids, and standard deviation.

The system includes a first computer configured to send and receive signals to the light source and light detector, and which is also configured to display the resultant total measured suspended solids value. Additionally, the system includes the computer program product, associated with the light source and light detector, and stored on a tangible computer memory media and operable on the computer. The computer program product includes a set of instructions which, when executed by the computer, cause the computer to perform various operations related to controlling and providing instructions to the various peripheral devices connected to the system. The computer receives an indication that the hydrocarbon liquid sample, which includes suspended solids therein, is positioned in the sample holder and ready to be measured. In one embodiment, the sample holder includes a sensor that can detect when the hydrocarbon liquid sample has been placed therein. In other embodiments, an operator signals to the computer that the sample has been placed in the sample holder and is ready to be analyzed. In response to the computer receiving an indication that the sample has been positioned in the sample holder, the computer sends a signal to the light source to illuminate the hydrocarbon liquid sample. The light source is positioned such that the light source is capable of illuminating the sample holder, wherein the illumination of the sample holder results in the light contacting the solids suspended in the sample and creating the scattered light pattern. The computer receives a signal from the light detector, wherein the signal is a measure of the collected scattered light. The signal from the light detector corresponds to the volume of suspended solids in the hydrocarbon liquid sample resulting from the measurement the scattered light by the light detector. The step of measuring the scattered light is responsive to an indication received by the light detector from the computer that the sample is being illuminated with the light source. The light detector can be located proximate to the sample holder and operable to measure the light scattered by the suspended particles. The computer correlates the signal from the light detector to the mass of total suspended solids in the hydrocarbon liquid sample, by correlating the signal in a step that includes utilizing a predetermined average density of the suspended solid particles. The computer communicates the mass of total suspended solids in the hydrocarbon liquid sample to the operator.

In another aspect, a computer program product, is provided that includes a set of instructions that, when executed by the computer, cause the computer to perform the following operations. The computer receives instructions that the hydrocarbon liquid sample containing suspended solids therein is positioned in the sample holder and ready to be measured. The computer then signals the light source to illuminate the hydrocarbon liquid sample with the light source, wherein the step of sending of the signal to the light source is made in response to the computer receiving the instructions that the sample is positioned in the sample holder. The light source is positioned such that the light source is capable of illuminating the sample holder, such that the light from the light source contacts solids suspended in the hydrocarbon liquid sample to create a scattered light pattern. The computer receives a signal from the light detector, wherein the signal is a measure of the collected scattered light and corresponds to a volume of suspended solids in the liquid sample, resulting from the measurement the scattered light by the light detector. The step of measuring the scattered light is responsive to an indication received by the light detector from the computer that the sample is being illuminated with the light source. The light detector is located proximate to the sample holder and operable to measure the light scattered by the suspended particles. The computer correlates signal from the light detector to a mass of total suspended solids in the hydrocarbon liquid sample. The step of correlating the signal includes utilizing a predetermined average density of the suspended solid particles. The computer then communicates the mass of total suspended solids in the hydrocarbon liquid sample to the operator.

One major advantage to the present invention is that the total time to complete the analysis of a sample is dramatically decreased, as compared with the standard gravimetric method, without a loss of accuracy. Indeed, in certain embodiments, the laser particle counter method provides results that are at least as accurate as the operating procedures for the ASTM standard. This saves time and allows for the quality of the hydrocarbon being produced to be more closely monitored as the industry standard gravimetric technique is approximately 50 times slower than the present invention. Additionally, the reduced analysis time and reduced volumes of sample required for the laser particle counter method for the determination of total suspended solids means that the operator is exposed to smaller volumes of potentially hazardous liquids and exposed for a shorter period of time. Furthermore, the present invention is advantageous over the prior art because samples can be collected in ordinary glass containers or bottles, or can be done in-line, rather than requiring the expensive metallic container that is required for the industry standard gravimetric technique. Finally, the analysis technique of the present invention can be done on-site and does not require that samples be collected sent to an outside laboratory.

Referring to FIG. 1, an exemplary baseline curve for the correlating measurements made with the laser particle counter is provided. The curve can be established by analyzing aviation fuel samples that include suspended solids utilizing both the laser particle counting technique of the present invention and the industry standard gravimetric technique. Specifically, a baseline gravimetric sample is prepared and measured using the gravimetric technique to provide a gravimetric total suspended solids content (mg/L). Additionally, a baseline optical sample is prepared and measured utilizing the optical technique utilizing a laser particle counter, as described herein, to provide an optical total suspended solids content ($cm^3$/L). The results of the total suspended solids from the gravimetric method are plotted against the results from the laser particle counter method for samples having identical total suspended solids, thereby allowing for determination of the total suspended solids based upon the measured volume of suspended solids. The slope of the curve provides a calculated particulate density, which for this example was determined to be 1994 mg/$cm^3$, or about 1.994 g/$cm^3$. The calibration curve is depicted in FIG. 1 and the numerical values of the analyses are presented in Table 1.

TABLE 1

The calibration data

Total Suspended Solid, mg/L

| No | Gravimetric Method (mg/L) | Laser Counter Method ($\times 10^{-5}$ cm$^3$/L) |
|---|---|---|
| 1 | 0.04 | 2.54 |
| 2 | 0.06 | 3.33 |
| 3 | 0.07 | 4.63 |
| 4 | 0.10 | 6.21 |
| 5 | 0.12 | 6.15 |
| 6 | 0.15 | 7.97 |
| 7 | 0.19 | 9.52 |
| 8 | 0.20 | 8.98 |
| 9 | 0.24 | 12.3 |
| 10 | 0.26 | 12.5 |
| 11 | 0.32 | 15.5 |
| 12 | 0.52 | 25.3 |
| 13 | 1.30 | 65.9 |

Figure 2:
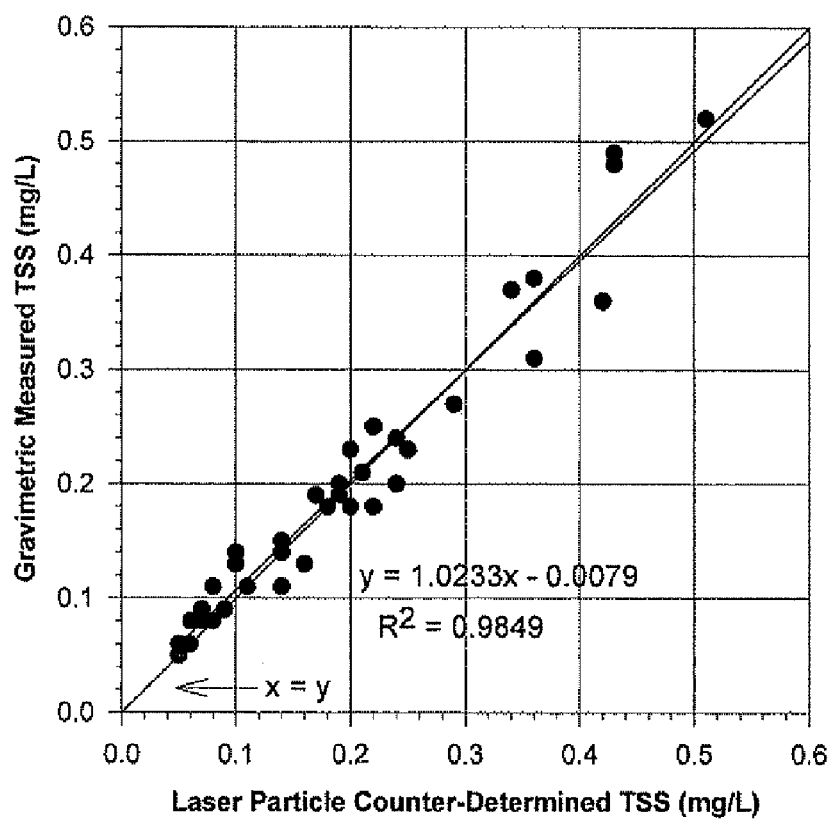
FIG. 2 shows a plot comparing gravimetric results and one method for determining total suspended solid content utilizing a laser particle counter according to one embodiment of the present invention.

Similarly, Table 2 provides a determination of the total suspended solids for selected aviation fuel sample (obtained from refueler nozzles and fuel hydrant systems at an airport) as determined by both the gravimetric and laser particle counter techniques. The total suspended solids for the sample measured by the gravimetric method was then compared with total suspended solids determined using the laser particle counter Referring to FIG. 2, a scatter plot comparing the results for both the gravimetric and laser particle counter techniques determined is provided. As shown in FIG. 2, excellent correlation is observed between gravimetric and laser particle counter methods, thus verifying the accuracy of the laser particle counter technique.

TABLE 2

Total Suspended Solid (TSS) content of jet fuel samples obtained by gravimetric and laser counter method.

| No | Gravimetric Method (mg/L) | Laser Counter Method (mg/L) | Error |
|---|---|---|---|
| 1 | 0.05 | 0.05 | 0.00 |
| 2 | 0.06 | 0.05 | 0.01 |
| 3 | 0.06 | 0.06 | 0.00 |
| 4 | 0.06 | 0.05 | 0.01 |
| 5 | 0.06 | 0.06 | 0.00 |
| 6 | 0.07 | 0.07 | 0.00 |
| 7 | 0.08 | 0.06 | 0.02 |
| 8 | 0.08 | 0.08 | 0.00 |
| 9 | 0.08 | 0.07 | 0.01 |
| 10 | 0.09 | 0.07 | 0.02 |
| 11 | 0.09 | 0.09 | 0.00 |
| 12 | 0.11 | 0.08 | 0.03 |
| 13 | 0.11 | 0.11 | 0.00 |
| 14 | 0.11 | 0.08 | 0.03 |
| 15 | 0.11 | 0.14 | −0.03 |
| 16 | 0.13 | 0.16 | −0.03 |
| 17 | 0.13 | 0.10 | 0.03 |
| 18 | 0.14 | 0.10 | 0.04 |
| 19 | 0.14 | 0.14 | 0.00 |
| 20 | 0.15 | 0.14 | 0.01 |
| 21 | 0.18 | 0.18 | 0.00 |
| 22 | 0.18 | 0.18 | 0.00 |
| 23 | 0.18 | 0.22 | −0.04 |
| 24 | 0.18 | 0.20 | −0.02 |
| 25 | 0.19 | 0.19 | 0.00 |
| 26 | 0.19 | 0.17 | 0.02 |
| 27 | 0.20 | 0.19 | 0.01 |
| 28 | 0.20 | 0.24 | −0.04 |
| 29 | 0.21 | 0.21 | 0.00 |
| 30 | 0.23 | 0.20 | 0.03 |
| 31 | 0.23 | 0.25 | −0.02 |
| 32 | 0.24 | 0.24 | 0.00 |
| 33 | 0.25 | 0.22 | 0.03 |
| 34 | 0.27 | 0.29 | −0.02 |
| 35 | 0.31 | 0.36 | −0.05 |
| 36 | 0.36 | 0.42 | −0.06 |
| 37 | 0.37 | 0.34 | 0.03 |
| 38 | 0.38 | 0.36 | 0.02 |
| 39 | 0.48 | 0.43 | 0.05 |
| 40 | 0.49 | 0.43 | 0.06 |
| 41 | 0.52 | 0.51 | 0.01 |

Referring to Table 2 and FIG. 2, comparison of the results for the determination of the total suspended solids as obtained by the laser particle counter method and the gravimetric method show a maximum deviation about 0.06 mg/L, and an average deviation of about 0.02 mg/L. This deviation of the laser particle counter method is within acceptable limits, within the accuracy of the gravimetric method, and makes it possible to provide reliable results for the actual content of the TSS in the jet fuel.

Figure 3:
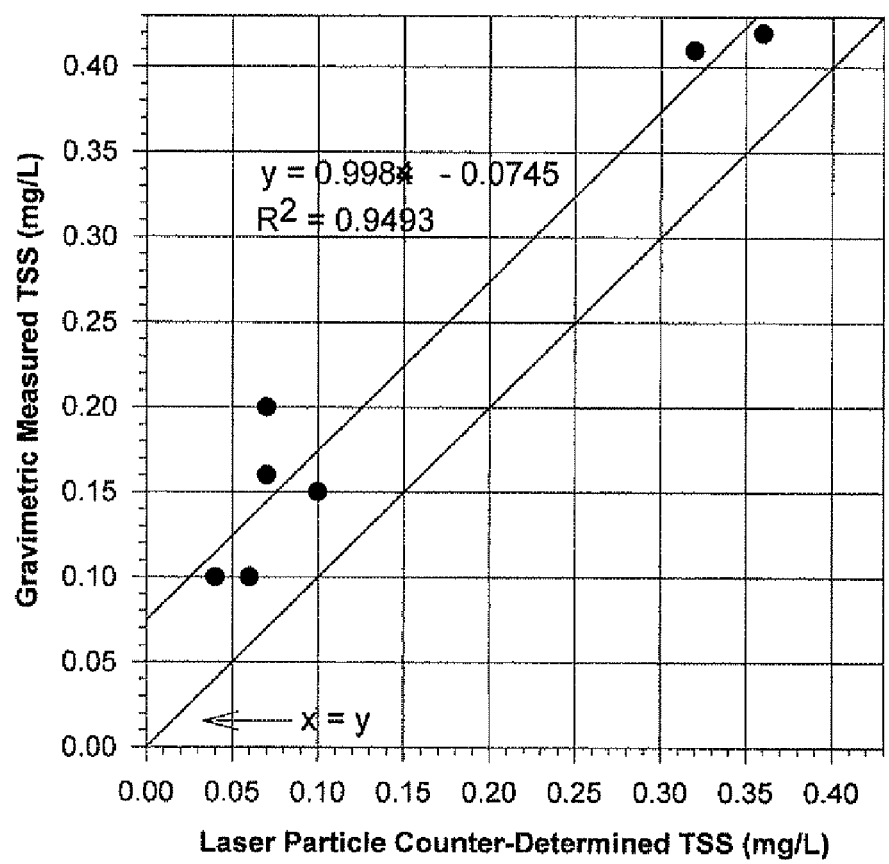
FIG. 3 shows a plot comparing gravimetric results and one method for determining total suspended solid content utilizing a laser particle counter according to one embodiment of the present invention
Figure 4:
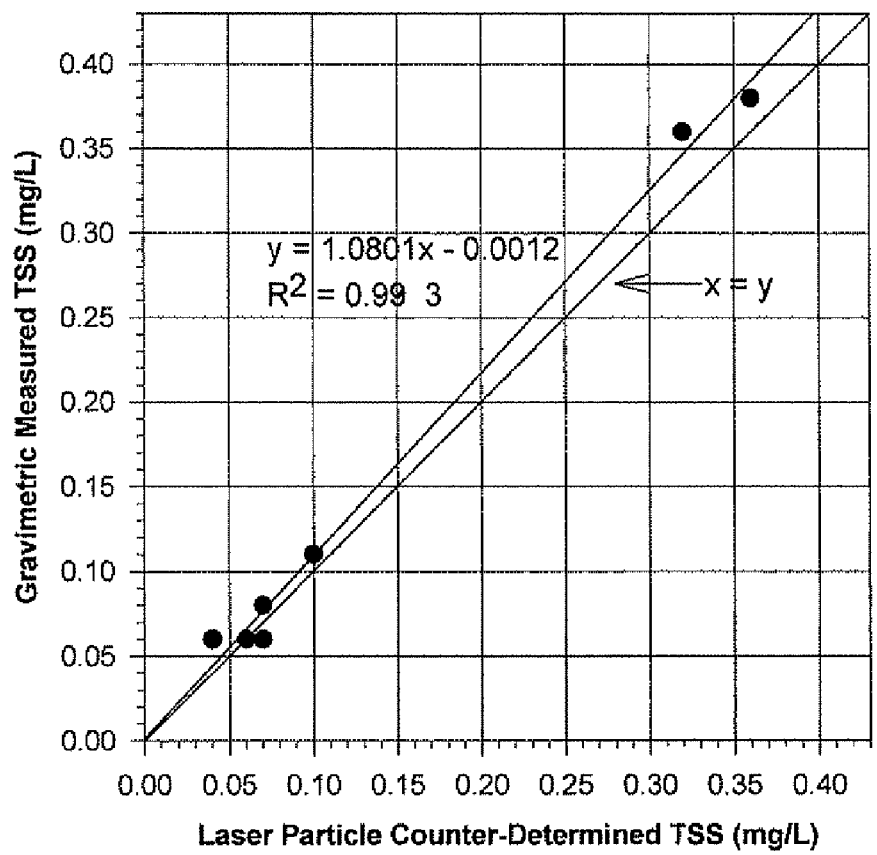
FIG. 4 shows a plot comparing gravimetric results and one method for determining total suspended solid content utilizing a laser particle counter according to one embodiment of the present invention in which the Dixon outlier test is applied.
Figure 5:
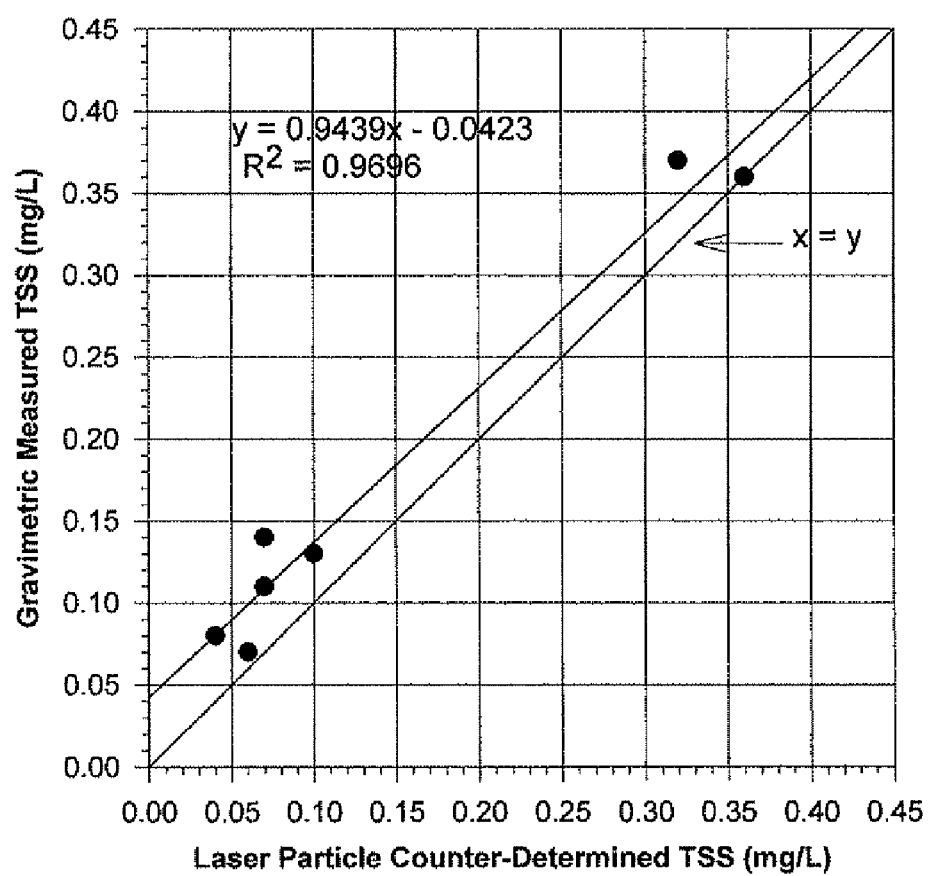
FIG. 5 shows a plot comparing gravimetric results and one method for determining total suspended solid content utilizing a laser particle counter according to one embodiment of the present invention in which the Box outlier test is applied.

In certain embodiments, a statistical method can be employed in addition with the laser particle counter method to provide improved accuracy. By applying one or more statistical methodology to the results of the laser particle counter technique data points that are determined to be statistical outliers can be omitted from the results. In certain embodiments, one or more statistical method can be applied to the calibration run to remove any data points that are statistical outliers. This provides a more accurate calculation of the total solids in the liquid. When applied, the statistical techniques typically remove results that show a sufficiently large deviation from the remaining results. Dixon and box plot tests for outlier were utilized and applied for the results obtained by the laser particle counter technique. These results are provided in Table 3, which compares the laser counting method raw data with the data after the Dixon and box plot tests have been applied. As shown in FIGS. 3, 4 and 5, the accuracy of the results was improved after the application of one or more of the statistical methods for the removal of outlier data points.

TABLE 3

Total Suspended Solid (TSS) content of jet fuel samples obtained by gravimetric
and laser counter method with the application of the outlier tests

| | Gravimetric Method | Laser Counter Method (mg/L) | | | Error | | |
|---|---|---|---|---|---|---|---|
| No | (mg/L) | WOASOT* | Dixon | Boxplot | WOASOT* | Dixon | Boxplot |
| 1 | 0.04 | 0.10 | 0.06 | 0.08 | −0.06 | −0.02 | −0.04 |
| 2 | 0.06 | 0.10 | 0.06 | 0.07 | −0.04 | 0.00 | −0.01 |
| 3 | 0.07 | 0.16 | 0.06 | 0.11 | −0.09 | 0.01 | −0.04 |
| 4 | 0.07 | 0.20 | 0.08 | 0.14 | −0.13 | −0.01 | −0.07 |
| 5 | 0.10 | 0.15 | 0.11 | 0.13 | −0.05 | −0.01 | −0.03 |
| 6 | 0.32 | 0.41 | 0.36 | 0.38 | −0.09 | −0.04 | −0.06 |
| 7 | 0.36 | 0.42 | 0.38 | 0.36 | −0.06 | −0.02 | 0.00 |

*Result without applying the statistical outlier test.

The calibration routine, i.e., the calculation of the true density value of the particulate matter, is not utilized for other techniques. Generally, to calculate the true density value, the total suspended solids are directly correlated to the optical data. Whereas other optical techniques that are employed for a determination of total suspended solids require frequent recalibration, depending upon the source of the aviation fuel, the present technique, on the other hand, only requires one calibration of the true density value for the solids.

The general equation for calculating the total suspended solids present in a liquid using a laser particle counter is provided as follows:

$$TSS_{LPC} = \frac{\sum_{i=1}^{n} \rho_i v_i}{v_j} \quad (1)$$

wherein $\rho_i$ and $v_i$ are the density and volume of each individual particle present in the aviation fuel, respectively, and $v_j$ is the volume of the aviation fuel in the sample. Assuming that the density of each particle is the same and using fixed jet fuel volume, the equation (1) can be rewritten as follows:

$$TSS_{LPC} = \frac{\rho_i}{v_j} \sum_{i=1}^{n} v_i \quad (2)$$

Equation (2) can then be used to estimate the total suspended solids, which is uncorrected value that depends on the estimated density value for the suspended solids which is difficult to obtain. Any error in the assumed density of the suspended particles further compounds the error in the determination of the total suspended solids therein.

In certain embodiments, the estimated total suspended solids values measured by the laser particle counter technique can be corrected to give more accurate values by determination of the slop and intercept of the calibration curve plot. The total suspended solids of aviation fuel samples were determined by using both the gravimetric and laser particle counter techniques. The total suspended solids values were used to prepare a calibration curve. The calibration curve is then analyzed to provide the equation for the line. To compensate for the arbitrarily approximated value for the particulates density of the suspended solids, the total suspended solids are calculated according to the following equation, which utilized a calculated density value for the solids present, and allows for quantitative calculations of the actual total suspended solids in the aviation fuel:

$$TSS_{LPC}^{Corr} = mTSS_{LPC} + b \quad (3)$$

Where m is the determined density of the particulates and b is the intercept, which are determined from the correlation curve of the gravimetric measured suspended solids values versus their corresponding values determined by the laser particle counter as shown in the equation (4) below.

$$TSS_{gravimetric} = mTSS_{LPC} + b \quad (4)$$

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

That which is claimed is:

1. A method for the quantitative determination of solid particles in a hydrocarbon liquid, the method comprising the step of:

providing a hydrocarbon liquid sample that includes solid particles suspended therein;

illuminating the solid particles with a light source;

detecting light scattered by solid particles;

correlating the scattered light to a total solids content of the hydrocarbon liquid sample to determine a calculated total suspended solids, applying a correction factor to the calculated total suspended solids to determine a corrected total suspended solids, wherein the correction factor is determined by comparing results from a gravimetric determination of total solids in a hydrocarbon liquid sample and an optical determination of the volume of total solids in a hydrocarbon liquid sample.

2. The method of claim 1 wherein the light source is a laser.

3. The method of claim 1 wherein the scattered light is detected with a photodiode.

4. The method of claim 3 wherein said photodiode produces a signal, said signal corresponding to a volume of solid particles in the hydrocarbon liquid sample.

5. The method of claim 1 wherein the hydrocarbon liquid includes an immiscible fluid.

6. The method of claim 5 further comprising the step of adding a masking agent to the hydrocarbon liquid sample, wherein said masking agent is miscible with the hydrocarbon liquid and the immiscible fluid.

7. The method of claim 1 further comprising rotating the light source about the hydrocarbon liquid sample.

8. The method of claim 1 further comprising rotating the light source and the detector about the hydrocarbon liquid sample.

9. The method of claim 1 wherein the light source and detector are rotated about the hydrocarbon liquid sample at a constant rate.

10. A method for determining the amount of solids in a hydrocarbon liquid that contains solid particles suspended therein, comprising the steps of:
   providing a hydrocarbon liquid sample of known volume, said hydrocarbon liquid sample comprising an unknown quantity of solids suspended therein;
   subjecting the hydrocarbon liquid sample to a light source, such that light from the light source scatters as a result of contacting the solid particles suspended in the hydrocarbon liquid sample;
   detecting the scattered light with a photodetector, said photodetector producing a signal corresponding to the scattered light;
   correlating the signal produced by the photodetector to a volume of solid particles suspended in the hydrocarbon liquid sample; and
   subjecting the signal to a correction factor, said correction factor providing a mass for the solid particle suspended in the hydrocarbon liquid.

11. The method of claim 10 wherein the hydrocarbon liquid is aviation fuel.

12. The method of claim 10 wherein the light source is a laser diode.

13. The method of claim 10 further comprising rotating the light source about the hydrocarbon liquid sample.

14. The method of claim 10 wherein the scattered light is collected by a photodetector.

15. The method of claim 10 further comprising rotating both the light source and the photodetector about the hydrocarbon liquid sample.

16. A system for determining total suspended solids in a hydrocarbon liquid, the system comprising:
   a first computer, a light source, a light detector and a sample holder, the first computer configured to send and receive signals to a light source and light detector, and to display a resultant total measured suspended solids value;
   a computer program associated with the light source and light detector, stored on a tangible computer memory media and operable on a computer, the computer program product comprising a set of instructions that, when executed by the computer, cause the computer to perform the operations of:
      receiving, by the computer, an indication that a hydrocarbon liquid sample containing suspended solids therein is positioned in the sample holder and ready to be measured;
      sending a signal from the computer to the light source to illuminate the liquid sample with the light source, responsive to the computer receiving the indication that the hydrocarbon liquid sample is positioned in the sample holder, the light source being positioned such that the light source is capable of illuminating the sample holder, wherein light that contacts solids that are suspended in the sample creates a scattered light pattern;
      receiving, by the computer, a signal from the light detector, wherein the signal is a measure of the collected scattered light, said signal corresponding to a volume of suspended solids in the hydrocarbon liquid sample, said signal resulting from the measurement the scattered light by the light detector, wherein the step of measuring the scattered light is responsive to an indication received by the light detector from the computer that the hydrocarbon liquid sample is being illuminated with the light source, said light detector being proximate to the sample holder and operable to measure the light scattered by the suspended particles;
      correlating the signal from the light detector to a mass of total suspended solids in the hydrocarbon liquid sample by the computer, the step of correlating the signal comprising utilizing a predetermined average density of the suspended solid particles; and
      communicating by the computer the mass of total suspended solids in the hydrocarbon liquid sample to an operator.

17. A computer program product, stored on a tangible computer memory media, operable on a computer, the computer program product comprising a set of instructions that, when executed by the computer, cause the computer to perform the operations of:
   receiving by a computer instructions that a liquid sample containing suspended solids therein is positioned in a sample holder and ready to be measured;
   sending a signal from the computer to the light source to illuminate the hydrocarbon liquid sample with the light source responsive to the computer receiving the instructions that the sample is positioned in the sample holder, the light source being positioned such that the light source is capable of illuminating the sample holder, wherein light that contacts solids that are suspended in the sample creates a scattered light pattern;
   receiving, by the computer, a signal from the light detector, wherein the signal is a measure of the collected scattered light, said signal corresponding to a volume of suspended solids in the hydrocarbon liquid sample, said signal resulting from the measurement the scattered light by the light detector, wherein the step of measuring the scattered light is responsive to an indication received by the light detector from the computer that the sample is being illuminated with the light source, said light detector being proximate to the sample holder and operable to measure the light scattered by the suspended particles;
   correlating the signal from the light detector to a mass of total suspended solids in the hydrocarbon liquid sample by the computer, the step of correlating the signal comprising utilizing a predetermined average density of the suspended solid particles; and communicating by the computer the mass of total suspended solids in the hydrocarbon liquid sample to an operator.

18. The method of claim 17 wherein the average density of the suspended solid particles is calculated by applying a correction factor, wherein said correction factor is determined by correlating a gravimetric determination of a total mass suspended solids and an optical determination of total volume of suspended solids in a hydrocarbon liquid sample.

* * * * *